United States Patent
Kotwica et al.

(10) Patent No.: US 6,579,419 B1
(45) Date of Patent: Jun. 17, 2003

(54) METHOD FOR PURIFYING NORBORNENE BY DISTILLATION

(75) Inventors: Roland Kotwica, Pontpoint (FR); André Marbach, Verneuil en Halatte (FR)

(73) Assignee: Elf Atochem, S.A., Puteau (FR)

( * ) Notice: Subject to any disclaimer, the term of this patent is extended or adjusted under 35 U.S.C. 154(b) by 0 days.

(21) Appl. No.: 09/555,671

(22) PCT Filed: Nov. 23, 1998

(86) PCT No.: PCT/FR98/02495

§ 371 (c)(1),
(2), (4) Date: Jul. 7, 2000

(87) PCT Pub. No.: WO99/28279

PCT Pub. Date: Jun. 10, 1999

(30) Foreign Application Priority Data

Dec. 2, 1997 (FR) .............................. 97 15161

(51) Int. Cl.[7] .............................. B01D 3/00; C07C 7/04
(52) U.S. Cl. .......................... 203/82; 203/84; 585/318; 585/353; 585/361; 585/802
(58) Field of Search .................. 203/73, 29, 74, 203/75, 100, 77, 78, 82, 84; 585/361, 353, 800, 802, 318

(56) References Cited

U.S. PATENT DOCUMENTS 3,007,977 A  11/1961  Hill et al. .................. 585/318
4,205,192 A * 5/1980  Harada ....................... 585/363
5,191,062 A * 3/1993  Bernier et al. .............. 585/803
5,565,069 A * 10/1996 Oi et al. ....................... 203/80

FOREIGN PATENT DOCUMENTS

| DE | 2425290 | * 12/1975 |
| DE | 215526  |   11/1984 |
| DE | 237987  |   8/1986  |

* cited by examiner

Primary Examiner—Virginia Manoharan
(74) Attorney, Agent, or Firm—Millen, White, Zelano & Branigan, P.C.

(57) ABSTRACT

For the purification of the norbornene obtained by the reaction of dicyclopentadiene or cyclopentadiene and ethylene, the crude reaction mixture containing light impurities having boiling temperatures lower than that of norbornene; medium-heavy impurities having the boiling temperatures between that of norbornene and that of ethylnorbornene; and heavy impurities containing ethylnorbornene and compounds boiling higher than ethylnorbornene, boiling temperatures greater than that ethylnorbornene, a first distillation of the crude reaction mixture is carried out in a tailing column (C1), removing a portion of the heavy impurities and a portion of the medium-heavy impurities; then a second distillation of the crude mixture, thus tailed, is carried out in a topping column (C2), removing the light impurities; and a third distillation of the mixture, thus topped, is subsequently carried out in a tailing column (C3), removing the remainder of the heavy and medium-heavy impurities.

18 Claims, 1 Drawing Sheet

METHOD FOR PURIFYING NORBORNENE BY DISTILLATION

FIELD OF THE INVENTION

The present invention relates to a process for the purification of norbornene by distillation.

BACKGROUND OF THE INVENTION

The synthesis of norbornene from dicyclopentadiene (DCPD) or cyclopentadiene (CPD) and ethylene gives a crude norbornene comprising impurities such as DCPD, dimethanooctahydronaphthalene (DMON), CPD and the like (these impurities will be described in more detail hereinbelow). The separation of these impurities from the norbornene is complicated because of the numerous equilibrium reactions existing between these products: any distillation of a crude synthetic product results in a reactive distillation.

U.S. Pat. No. 3,007,977 discloses a process for the purification of norbornene from a reaction mixture obtained by reaction of ethylene with CPD and DCPD, the said reaction mixture comprising unreacted CPD and norbornene. This process comprises the stages consisting in:

- in a first fractionation region, fractionating the said reaction mixture in order to obtain, as intermediate fraction, norbornene with minor amounts of CPD and to discharge the DCPD from the said fractionation region;
- in a second fractionation region, fractionating the said intermediate fraction into a top fraction comprising CPD and norbornene and into a fraction comprising essentially norbornene.

In accordance with this U.S. Pat. No. 3,007,977, recourse is thus had, for the purification of a crude product from the synthesis of norbornene, to a system based on two distillation columns; this system is a base system in which the norbornene is successively tailed and then topped.

However, the effectiveness of such a system is not very high because of the DCPD/CPD equilibrium. This is because the CPD formed in the first column during the heating of the charge is found in the top fraction. As the temperature of the second distillation column is lower, the reverse reaction results in a norbornene comprising residual heavy products, such as DCPD, DMON, and the like. Furthermore, the product obtained in this column bottom is coloured, which limits its applications.

French Patent Application FR-A-2,438,639 discloses a process for the manufacture of norbornene from the products of the reaction from the synthesis of norbornene between DCPD or CPD and ethylene:

- in accordance with a first embodiment (illustrated by FIG. 1 of FR-A-2,438,639), the crude synthetic product is introduced into a first distillation column, the top product of which is, after condensation, reacted at 70° C. with a mean residence time of one hour, in order to dimerize the CPD into DCPD, and is then reintroduced into the column. The mixture of the products which falls into the column bottom at 105° C. is introduced into a second distillation column, the product comprising the norbornene being evaporated and all the heavy compounds being withdrawn as column bottom product;
- in accordance with a second embodiment (illustrated by FIG. 2 of FR-A-2,438,639), the crude synthetic product is introduced into a first distillation column where, at 112° C. and with a mean residence time of approximately 30 hours, a large portion of the product comprising the norbornene is evaporated, the heavy components, comprising a very high proportion of norbornene, being withdrawn as column bottom products. The top product is conveyed into a second distillation column where norbornene, still comprising dicyclopentadiene fractions, is obtained at the top and where norbornene of high purity is obtained at the bottom.

The disadvantage of the two systems described hereinabove, without topping, is the presence of light impurities, such as isoprene, resulting from the starting DCPD, which impurities are not separated from the norbornene. This presence of impurities necessitates the use of special grades of DCPD if it is desired to obtain norbornene of high purity.

In the processes according to U.S. Pat. No. 3,007,977 and FR-A-2,438,639, the purity obtained for the norbornene is a function not only of the reflux ratios and of the temperatures but also of the overall charge of the columns. This is because the monomerization of the DCPD is not immediate, so that the composition is also influenced by the residence times of the products in the columns.

An aim of the present invention is to provide a process for the purification of the norbornene by distillation which does not have any of the disadvantages of the processes of the prior art and which makes it possible to operate industrially for the production of a norbornene of satisfactory quality.

In accordance with the present invention, this aim is achieved, in other words a consistent quality of norbornene as far as possible free from residual heavy and light products can be obtained, without excessive loss of product, by a process involving three successive distillation columns.

SUMMARY OF THE INVENTION

The process according to the present invention for the purification of the norbornene obtained by the reaction of dicyclopentadiene or cyclopentadiene and ethylene, the crude reaction mixture comprising:

- light impurities, the boiling temperatures of which are lower than that of norbornene;
- medium-heavy impurities, the boiling temperatures of which are between that of norbornene and that of ethylnorbornene; and
- heavy impurities, the boiling temperatures of which are greater than that of ethylnorbornene, the latter furthermore being included in the said heavy impurities, is characterized in that a first distillation of the crude reaction mixture is carried out in a tailing column (C1), removing a portion of the heavy impurities and a portion of the medium-heavy impurities; then a second distillation of the crude mixture, thus tailed, is carried out in a topping column (C2), removing the light impurities; and a third distillation of the mixture, thus topped, is subsequently carried out in a tailing column (C3), removing the remainder of the heavy and medium-heavy impurities.

Furthermore, the recombination of the cyclopentadiene to dicyclopentadiene, which begins in the tailing column (C1) and is continued in the topping column (C2), can be continued in a tank (R) interposed between the topping column (C2) and the second tailing column (C3).

In a particularly preferred way, the bottom flow from the second tailing column (C3) is recycled at the inlet of the first tailing column (C1).

BRIEF DESCRIPTION OF THE DRAWING

The three distillation columns (C1), (C2) and (C3) are depicted on the single FIGURE of the appended drawing, which is a schematic flowsheet.

Column (C1)

Figure 1:
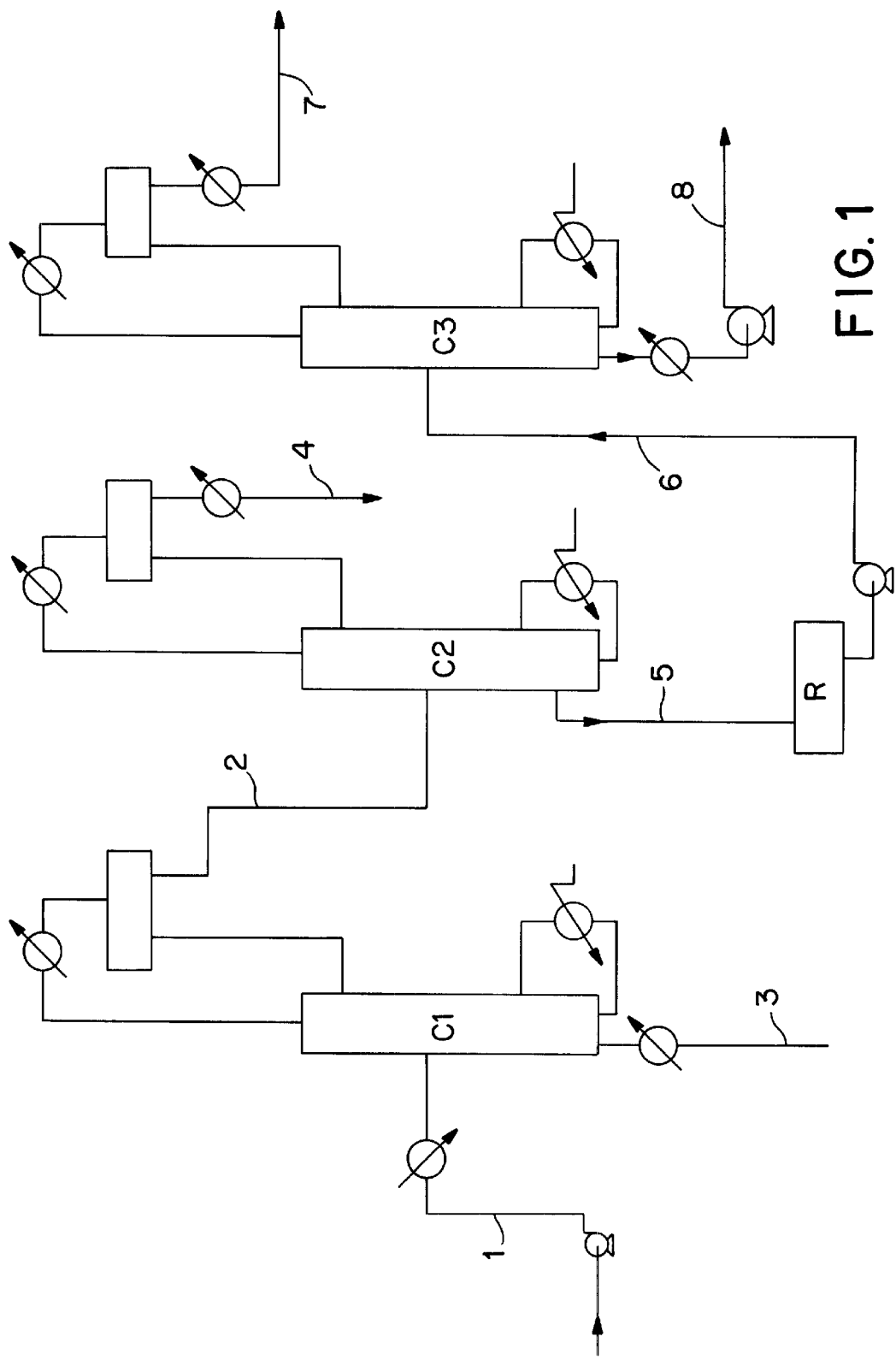

The aim of this column, filled with packing units, is to remove a portion of the heavy products and of the medium-heavy products; it is fed with a flow (1) of crude norbornene which assay is approximately 85 to 98%, according to the grade of the DCPD or of the CPD/DCPD reacted and the operating conditions for the synthesis (molar ratio, flow rate). The impurities, a list of which will be found in Tables 1 and 2 hereinbelow, are classified as:

light impurities, representing 0.1–1%;
medium-heavy impurities, representing 0.1–1%; and
heavy impurities, representing 1–15% (for a total of 100%).

This column (C1) operates at atmospheric pressure with a bottom temperature of 100 to 160° C. and a top temperature of 95 to 110° C.

A flow (2) is obtained at the top of column (C1), which flow has the following composition (for 100%):

0.1–2% of light products;
0.1–2% of medium-heavy products; and
0–0.2% of heavy products, the remainder being composed of norbornene.

A flow (3) is removed at the bottom of column (C1), which flow has the following composition (for 100%):

0–1% of light products;
1–5% of medium-heavy products; and
50–80% of heavy products, the remainder being composed of norbornene.

This column (C1) makes it possible to remove, for example, in the flow (3), approximately 25–75% of the medium-heavy methylnorbornenes, which are due to methylcyclopentadiene, a conventional and inevitable impurity of CPD, and approximately 95–99% of the heavy products (recombination of CPD to DCPD).

Column (C2) and Tank (R)

The aim of the column (C2), filled with packing units, is to remove most of the light products.

This column operates at atmospheric pressure with a bottom temperature of 95–100° C. and a top temperature of 94–100° C.

A flow (4) is obtained at the top, which flow has the following composition (for 100%):

2–10% of light products;
0–0.2% of medium-heavy-products; and
0–0.5% of heavy products, the remainder being composed of norbornene.

The flow (6) exiting from the tank (R) downstream of the column (C2) has the following composition (for 100%):

0–0.1% of light products;
0–0.5% of medium-heavy products; and
0–0.1% of heavy products, the remainder being composed of norbornene.

Column (C3)

The aim of this column, filled with packing units, is to remove the remainder of the heavy products and of the medium-heavy products (methylnorbornenes).

It operates at atmospheric pressure with a bottom temperature of 95–100° C. and with a top temperature of 95–100° C.

The desired flow (7) is obtained at the top, which flow has the following composition (for 100%):

0–0.1% of light products;
0–0.5% of medium-heavy products; and
0–0.1% of heavy products, the remainder being composed of norbornene.

The flow (8) of the heavy products and of the medium-heavy products is obtained at the bottom, which flow is recycled in the flow (1) and has the following composition (for 100%):

0–0.1% of light products;
1–10% of medium-heavy products; and
0–0.5% of heavy products, the remainder being composed of norbornene.

Thus, the process according to the present invention makes it possible to obtain a better quality of norbornene than that of the prior processes, with the additional advantage that this higher purity is obtained with little in the way of losses.

The following examples illustrate the present invention without, however, limiting the scope thereof. In these examples, the percentages are also given by weight.

EXAMPLE 1

600 kg/h of a flow (1), the composition of which is given in Table 1, are conveyed into the column (C1), which column operates at atmospheric pressure, at a bottom temperature of 132° C. and at a top temperature of 98° C. A portion of the distilled flow is returned at the top of column (C1), so as to provide a draw-off ratio of 0.86.

The compositions of the top flow (2) (564 kg/h) and of the bottom flow (3) (36 kg/h) are also given in Table 1.

The flow (2) (564 kg/h) is sent to the distillation column (C2), which column operates at atmospheric pressure, at a top temperature of 94° C. and at a bottom temperature of 97° C. A portion of the distilled flow is returned at the top of column (C2), so as to provide a reflux/draw-off ratio of 20.97.

The composition of the top flow (4) (31 kg/h) is also given in Table 1.

The flow (6) exiting from the tank (R) (533 kg/h) has a composition also given in Table 1.

The flow (6) is sent to the distillation column (C3), which column operates at atmospheric pressure, at a top temperature of 98° C. and at a bottom temperature of 99° C. A portion of the distilled flow is returned at the top of column (C3), so as to provide a reflux/draw-off ratio of 1.67.

The compositions of the top flow (7) (430 kg/h) and of the bottom flow (8) (103 kg/h) are given in Table 1.

EXAMPLE 2

740 kg/h of a flow (1), the composition of which is given in Table 2, are conveyed into the column (C1), which column operates at atmospheric pressure, at a bottom temperature of 130° C. and at a top temperature of 99° C.

A portion of the distilled flow is returned at the top of column (C1), so as to provide a draw-off ratio of 0.89.

The compositions of the top flow (2) (682 kg/h) and of the bottom flow (3) (58 kg/h) are also given in Table 2.

The flow (2) (682 kg/h) is sent to the distillation column (C2), which column operates at atmospheric pressure, at a top temperature of 95.5° C. and at a bottom temperature of 95.5° C. A portion of the distilled flow is returned at the top of column (C2), so as to provide a reflux/draw-off ratio of 26.79.

The composition of the top flow (4) (28 kg/h) is also given in Table 2.

The flow (6) exiting from the tank (R) (654 kg/h) has a composition also given in Table 2.

The flow (6) is sent to the distillation column (C3), which column operates at atmospheric pressure, at a top temperature of 99° C. and at a bottom temperature of 100° C. A portion of the distilled flow is returned at the top of column (C3), so as to provide a reflux/draw-off ratio of 1.13.

The compositions of the top flow (7) (610 kg/h) and of the bottom flow (8) (44 kg/h) are given in Table 2.

TABLE 1

| Composition (% by weight) | Column C1 | | | Column C2 | | Column C3 | |
|---|---|---|---|---|---|---|---|
| | Feed (1) | Top (2) | Bottom (3) | Top (4) | Bottom* (6) | Top (7) | Bottom (8) |
| Ethylene + ethane | 0.0444 | 0.0251 | 0 | 0.0402 | 0 | 0 | 0 |
| 2-Methyl-1,3-butadiene | 0.0446 | 0.0481 | 0 | 0.7842 | 0 | 0 | 0 |
| Cyclopentadiene (CPD) | 0.2246 | 0.2939 | 0.0067 | 3.8897 | 0.0003 | 0.0003 | 0.0007 |
| cis-1,3-Pentadiene | 0.0538 | 0.0632 | 0 | 1.0147 | 0 | 0 | 0 |
| 2-Methylcyclopentadiene | 0.0011 | 0.0009 | 0 | 0.0164 | 0 | 0 | 0 |
| Benzene | 0.011 | 0.0121 | 0 | 0.1356 | 0.0041 | 0.0057 | 0.0003 |
| Cyclohexene | 0.0074 | 0.0081 | 0 | 0.0364 | 0.006 | 0.0076 | 0.001 |
| Other light products | 0.0418 | 0.0657 | 0.0009 | 0.8553 | 0.0003 | 0.0014 | 0.0023 |
| Total Light Impurities | 0.4287 | 0.5171 | 0.0076 | 6.7725 | 0.0107 | 0.015 | 0.0043 |
| Norbornene | 93.3247 | 98.9023 | 26.9426 | 92.95 | 99.316 | 99.7461 | 97.85 |
| 4-Methyl- and 3-methylcyclohexene | 0.0378 | 0.0295 | 0.0221 | 0.0152 | 0.0296 | 0.0201 | 0.0565 |
| 1-Methylnorbornene | 0.1643 | 0.1614 | 0.206 | 0.0366 | 0.1698 | 0.0884 | 0.4187 |
| 5-Methylnorbornene | 0.003 | 0.0021 | 0.0144 | 0 | 0.0022 | 0.0005 | 0.0082 |
| 6-Methylnorbornene | 0.0034 | 0.0022 | 0.0189 | 0 | 0.0025 | 0.0004 | 0.0085 |
| 2-Methylnorbornene | 0.3046 | 0.1892 | 1.6855 | 0.0119 | 0.2034 | 0.0213 | 0.756 |
| Other medium-heavy products | 0.17 | 0.1581 | 0.3921 | 0.0296 | 0.1652 | 0.0552 | 0.4694 |
| Total Medium-Heavy Impurities | 0.6831 | 0.5425 | 2.339 | 0.0933 | 0.5727 | 0.1859 | 1.7173 |
| exo-Dicyclopentadiene | 0.2049 | 0.0003 | 2.647 | 0.0028 | 0.0005 | 0 | 0.0025 |
| endo-Dicyclopentadiene | 0.5602 | 0.0105 | 6.7246 | 0.1739 | 0.0666 | 0 | 0.2773 |
| 5-Methyl- and 6-Methyltetrahydroindene | 1.5522 | 0.0008 | 19.8542 | 0 | 0.0009 | 0 | 0.0042 |
| Dimethanooctahydronaphthalene (DMON) | 2.0612 | 0.002 | 26.3626 | 0.0065 | 0.0064 | 0 | 0.02 |
| Other heavy products | 1.185 | 0.0244 | 15.1224 | 0.0015 | 0.0268 | 0.053 | 0.1249 |
| Total Heavy Impurities | 5.5635 | 0.038 | 70.7108 | 0.1847 | 0.1012 | 0.053 | 0.4289 |

*Flow exiting from the tank R

TABLE 2

| Composition (% by weight) | Column C1 | | | Column C2 | | Column C3 | |
|---|---|---|---|---|---|---|---|
| | Feed (1) | Top (2) | Bottom (3) | Top (4) | Bottom* (6) | Top (7) | Bottom (8) |
| Ethylene + ethane | 0.0148 | 0.0118 | 0 | 0.0202 | 0 | 0 | 0 |
| 2-Methyl-1,3-butadiene | 0.0273 | 0.0295 | 0 | 0.5563 | 0 | 0 | 0 |
| Cyclopentadiene (CPD) | 0.1372 | 0.1905 | 0.0056 | 2.6706 | 0.0005 | 0.0007 | 0.0003 |
| cis-1,3-Pentadiene | 0.0314 | 0.0344 | 0 | 0.6719 | 0 | 0 | 0 |
| 2-Methylcyclopentadiene | 0.0008 | 0.0011 | 0 | 0.0092 | 0.0002 | 0 | 0 |
| Benzene | 0.0081 | 0.009 | 0 | 0.0909 | 0.0036 | 0.0039 | 0 |
| Cyclohexene | 0.0058 | 0.0063 | 0 | 0.0286 | 0.0049 | 0.0052 | 0.0006 |
| Other light products | 0.0226 | 0.0537 | 0 | 0.5175 | 0.0005 | 0.0003 | 0 |
| Total Light Impurities | 0.248 | 0.3363 | 0.0056 | 4.5652 | 0.010 | 0.010 | 0.0009 |
| Norbornene | 93.2515 | 99.1425 | 31.0239 | 95.2365 | 99.4059 | 99.6207 | 93.7096 |
| 4-Methyl- and 3-methylcyclohexene | 0.0258 | 0.0263 | 0.0239 | 0.0122 | 0.0271 | 0.025 | 0.074 |
| 1-Methylnorbornene | 0.1775 | 0.17 | 0.2612 | 0.0407 | 0.1777 | 0.1502 | 0.7974 |
| 5-Methylnorbornene | 0.0029 | 0.0018 | 0.0151 | 0 | 0.0019 | 0.0008 | 0.0255 |
| 6-Methylnorbornene | 0.0033 | 0.0018 | 0.0197 | 0 | 0.0019 | 0.0006 | 0.0277 |
| 2-Methylnorbornene | 0.2943 | 0.1561 | 1.7726 | 0.0088 | 0.1664 | 0.0484 | 2.5119 |
| Other medium-heavy products | 0.1602 | 0.141 | 0.4263 | 0.0255 | 0.1461 | 0.1019 | 1.0849 |
| Total Medium-Heavy Impurities | 0.664 | 0.497 | 2.5188 | 0.0872 | 0.5211 | 0.3269 | 4.5214 |
| exo-Dicyclopentadiene | 0.273 | 0.0007 | 3.1324 | 0.007 | 0.0009 | 0 | 0.0151 |
| endo-bicyclopentadiene | 0.672 | 0.0023 | 7.5062 | 0.0976 | 0.037 | 0 | 1.2552 |
| 5-Methyl- and 6-Methyltetrahydroindene | 1.4154 | 0.0008 | 16.2856 | 0 | 0.0009 | 0 | 0.0217 |

TABLE 2-continued

|  | Column C1 | | | Column C2 | | Column C3 | |
| --- | --- | --- | --- | --- | --- | --- | --- |
| Composition (% by weight) | Feed (1) | Top (2) | Bottom (3) | Top (4) | Bottom* (6) | Top (7) | Bottom (8) |
| Dimethanooctahydronaphthalene (DMON) | 2.3095 | 0.0009 | 26.2671 | 0.0043 | 0.0031 | 0 | 0.0825 |
| Other heavy products | 1.1666 | 0.0195 | 13.2604 | 0.0022 | 0.0214 | 0.0423 | 0.3935 |
| Total Heavy Impurities | 5.8365 | 0.0242 | 66.4517 | 0.1111 | 0.0633 | 0.0423 | 1.768 |

*Flow exiting from tank R

What is claimed is:

1. A process for the purification of norbornene obtained by reaction of ethylene and at least one of dicyclopentadiene and cyclopentadiene resulting in a crude reaction mixture comprising:
light impurities, the boiling temperatures of which are lower than that of norbornene;
medium-heavy impurities, the boiling temperatures of which are between that of norbornene and that of ethylnorbornene; and
heavy impurities, the boiling temperatures of which are greater than that of ethylnorbornene, the latter being included in said heavy impurities,
wherein a first distillation of the crude reaction mixture (1) is carried out in a first tailing column (C1) having an inlet, removing a portion of the heavy impurities and a portion of the medium-heavy impurities; then a second distillation of the crude mixture, thus tailed, is carried out in a topping column (C2), removing the light impurities; and a third distillation of the mixture, thus topped, is subsequently carried out in a second tailing column (C3), removing the remainder of the heavy and medium-heavy impurities, and from said second tailing column (C3) recovering a top product of purified norbornene.

2. A process according to claim 1, wherein in the tailing column (C1) cyclopentadiene at least in part is converted to dicyclopentadiene, and is further converted in the topping column (C2), and is further converted in a tank (R) interposed between the topping column (C2) and the second tailing column (C3).

3. A process according to claim 2, wherein at least a partial bottom flow from the second tailing column (C3) is recycled at the inlet of the first tailing column (C1).

4. A process according to claim 1, wherein the first tailing column (C1) is operated at atmospheric pressure, at a bottom temperature of 100 to 160° C. and at a top temperature of 95 to 110° C.

5. A process according to claim 4, wherein the topping column (C2) is operated at atmospheric pressure, at a bottom temperature of 95 to 100° C. and at a top temperature of 94 to 100° C.

6. A process according to claim 5, wherein the second tailing column (C3) is operated at atmospheric pressure, at a bottom temperature of 95 to 100° C. and at a top temperature of 95 to 100° C.

7. A process according to claim 6, wherein at least a partial bottom flow from the second tailing column (C3) is recycled at the inlet of the first tailing column (C1).

8. A process according to claim 4, wherein the second tailing column (C3) is operated at atmospheric pressure, at a bottom temperature of 95 to 100° C. and at a top temperature of 95 to 100° C.

9. A process according to claim 1, wherein the topping column (C2) is operated at atmospheric pressure, at a bottom temperature of 95 to 100° C. and at a top temperature of 94 to 100° C.

10. A process according to claim 1, wherein the second tailing column (C3) is operated at atmospheric pressure, at a bottom temperature of 95 to 100° C. and at a top temperature of 95 to 100° C.

11. A process according to claim 1, wherein at least a partial bottom flow from the second tailing column (C3) is recycled at the inlet of the first tailing column (C1).

12. A process according to claim 1, wherein that the tailing column (C1) is fed with a flow (1) of crude norbornene with the composition:
0.1–1% of light impurities;
0.1–1% of medium-heavy impurities;
1–15% of heavy impurities,
the remainder being composed of norbornene, in order to separate:
at the top, a flow (2) with the composition:
0.1 to 2% of light impurities;
0.1 to 2% of medium-heavy impurities;
0 to 0.2% of heavy impurities,
the remainder being composed of norbornene; and
at the bottom, a flow (3) with the composition:
0 to 1% of light impurities;
1 to 5% of medium-heavy impurities;
50 to 80% of heavy impurities,
the remainder being composed of norbornene; in that the flow (2) is then conveyed into the topping column (C2), in order to separate:
at the top, a flow (4) with the composition:
2 to 10% of light impurities;
0 to 0.2% of medium-heavy impurities;
0 to 0.5% of heavy impurities,
the remainder being composed of norbornene; and
at the bottom, a flow (6) with the composition:
0 to 0.1% of light impurities;
0 to 0.5% of medium-heavy impurities;
0 to 0.1% of heavy impurities,
the remainder being composed of norbornene; and in that the flow (6) is then conveyed into the second tailing column (C3),
in order to separate:
at the top, the desired flow (7) with the composition:
0 to 0.1% of light impurities;
0 to 0.5% of medium-heavy impurities;
0 to 0.1% of heavy impurities,
the remainder being composed of norbornene; and
at the bottom, a flow (8) with the composition:
0 to 0.1% of light impurities;
1 to 10% of medium-heavy impurities;
0 to 0.5% of heavy impurities,
the remainder being composed of norbornene, the percentages being by weight and all the compositions being indicated for a total of 100%.

13. A process according to claim 12, wherein at least a partial bottom flow from the second tailing column (C3) is recycled at the inlet of the first tailing column (C1).

14. A process according to claim 12, wherein the first tailing column (C1) is operated at atmospheric pressure, at a bottom temperature of 100 to 160° C. and at a top temperature of 95 to 110° C.

15. A process according to claim 14, wherein the topping column (C2) is operated at atmospheric pressure, at a bottom temperature of 95 to 100° C. and at a top temperature of 94 to 100° C.

16. A process according to claim 15, wherein the second tailing column (C3) is operated at atmospheric pressure, at a bottom temperature of 95 to 100° C. and at a top temperature of 95 to 100° C.

17. A process according to claim 1, wherein the norbornene is obtained by reacting ethylene with a starting material comprising cyclopentadiene.

18. A process according to claim 1, wherein the norbornene is obtained by reacting ethylene with a starting material comprising a mixture of cyclopentadiene and dicyclopentadiene.

* * * * *